United States Patent
Tang et al.

(10) Patent No.: US 10,080,641 B2
(45) Date of Patent: Sep. 25, 2018

(54) URETERAL STENTS WITH WAVEFORM INTERLAYERS AND INTERSTITCHING

(71) Applicant: GYRUS ACMI, INC., Southborough, MA (US)

(72) Inventors: Hui Tang, Acton, MA (US); David Salto, Hopedale, MA (US)

(73) Assignee: GYRUS ACMI, INC., Southborough, MA (US)

( * ) Notice: Subject to any disclaimer, the term of this patent is extended or adjusted under 35 U.S.C. 154(b) by 42 days.

(21) Appl. No.: 14/962,654

(22) Filed: Dec. 8, 2015

(65) Prior Publication Data

US 2016/0089229 A1 Mar. 31, 2016

Related U.S. Application Data

(63) Continuation of application No. 14/077,807, filed on Nov. 12, 2013, now Pat. No. 9,242,079.

(51) Int. Cl.
*A61F 2/04* (2013.01)
*A61M 27/00* (2006.01)

(52) U.S. Cl.
CPC .............. *A61F 2/04* (2013.01); *A61M 27/008* (2013.01); *A61F 2002/048* (2013.01);
(Continued)

(58) Field of Classification Search
CPC .................. A61F 2/07; A61F 2002/072; A61F 2002/047; A61F 2/0063; A61F 2002/068; A61M 27/008
See application file for complete search history.

(56) References Cited

U.S. PATENT DOCUMENTS 5,913,896 A 6/1999 Boyle et al.
6,136,023 A 10/2000 Boyle
(Continued)

FOREIGN PATENT DOCUMENTS

JP 2002-537893 A 11/2002
JP 2007-524480 A 8/2007
WO 2006/023261 A2 3/2006

OTHER PUBLICATIONS

May 26, 2016 International Preliminary Report on Patentability issued in International Application PCT/US2014/063066.
(Continued)

*Primary Examiner* — Thomas J Sweet
*Assistant Examiner* — Daniel Bissing
(74) *Attorney, Agent, or Firm* — Oliff PLC

(57) ABSTRACT

Ureteral stents include a tubular body defining a lumen and have a distal kidney section, a proximal bladder section, and a ureter section between the distal and proximal sections. The tubular body has a first material layer and a stiffening member that extends through at least a portion of a length of the tubular body. The stiffening member has a stiffness characteristic that varies along its length. This enables different portions of the stent to have different stiffness characteristics that preferably are optimized for the location of those portions within the human body. The stiffening member may be at least a second material layer having a second stiffness that is different from a first stiffness of the first material layer, and/or at least one strand of material that is embedded within the first material layer.

9 Claims, 14 Drawing Sheets

(52) U.S. Cl.
CPC . *A61F 2210/0076* (2013.01); *A61F 2230/001* (2013.01); *A61F 2230/0006* (2013.01); *A61F 2230/0008* (2013.01); *A61F 2230/0017* (2013.01); *A61F 2230/0021* (2013.01); *A61F 2230/0023* (2013.01); *A61F 2250/0018* (2013.01); *A61F 2250/0029* (2013.01); *A61F 2250/0036* (2013.01)

(56) References Cited

U.S. PATENT DOCUMENTS

| | | | |
|---|---|---|---|
| 7,044,981 | B2 | 5/2006 | Liu et al. |
| 7,582,112 | B2 | 9/2009 | Scheuermann et al. |
| 7,678,154 | B2 | 3/2010 | McWeeney et al. |
| 7,789,915 | B2 | 9/2010 | Lavelle et al. |
| 8,790,777 | B2 * | 7/2014 | Kozar .............. B29C 70/083 264/122 |
| 2001/0047201 | A1 * | 11/2001 | Cox .................. A61F 2/91 623/1.16 |
| 2003/0074082 | A1 | 4/2003 | Bottcher et al. |
| 2004/0059279 | A1 | 3/2004 | McWeeney et al. |
| 2004/0131863 | A1 | 7/2004 | Belliveau et al. |
| 2005/0165366 | A1 | 7/2005 | Brustad et al. |
| 2005/0261763 | A1 | 11/2005 | Wang et al. |
| 2007/0207186 | A1 | 9/2007 | Scanlon et al. |
| 2007/0225679 | A1 | 9/2007 | Deal |
| 2008/0091275 | A1 * | 4/2008 | Ducharme .......... A61M 27/008 623/23.7 |
| 2010/0042202 | A1 | 2/2010 | Ramzipoor et al. |
| 2014/0052272 | A1 * | 2/2014 | Amos, Jr. .......... A61M 27/008 623/23.69 |
| 2015/0142127 | A1 * | 5/2015 | Ponsky .............. A61M 27/008 623/23.69 |

OTHER PUBLICATIONS

Jan. 26, 2015 International Search Report and Written Opinion issued in Application No. PCT/US2014/063066.

Jan. 26, 2018 Office Action issued in Chinese Patent Application No. 201480037399.9.

* cited by examiner

URETERAL STENTS WITH WAVEFORM INTERLAYERS AND INTERSTITCHING

CROSS REFERENCE TO RELATED APPLICATION

This application is a continuation application of U.S. patent application Ser. No. 14/077,807, filed Nov. 12, 2013, the contents of which are incorporated herein by reference.

BACKGROUND

The invention relates to ureteral stents.

A ureter is a tubular passageway in the body that conveys urine from a kidney to a bladder. Ureteral stents are used to facilitate urinary drainage from the kidney to the bladder in patients having a ureteral obstruction or injury, or to protect the integrity of the ureter in a variety of surgical manipulations. Ureteral stents are typically about 30 cm long, hollow catheter-like devices made from a polymer and placed within the ureter with the distal end residing in the kidney and the proximal end residing in the bladder. Ureteral stents function by channeling the flow of urine from the kidney to the bladder. One or both ends of a ureteral stent may be coiled in a pigtail shape to prevent the upward and/or downward migration of the stent due to patient movement. For example, the ureter may stretch up to 5 cm in either direction during a patient's normal bodily movements, such as movement during breathing. If the stent is not sufficiently anchored, this may result in stent migration and displacement.

Another factor to be considered relates to tissue irritation caused by the stent. A stent may cause tissue irritation due to the relative movement between the stent and the ureter during natural stretching of the ureter, even when the stent is properly anchored. A typical semi-rigid, anchored stent is unable to adjust for the natural extension and contraction of the ureter during bodily movements, resulting in pressure and irritation of the ureter and surrounding tissue.

Regions of tissue most vulnerable to stent-induced irritation include the kidney, the renal pelvis, the sensitive bladder tissue in the trigonal region, and tissue of the ureteral vesicle junction leading into the bladder. Irritation may be caused by the static or dynamic contact of the semi-rigid stent with sensitive tissues of the body, such as the kidney and the renal pelvis. Chronic trigonal tissue irritation may result from contact of tissue by the bladder-anchoring features of the stent, for example, pigtails at the stent ends. Irritation problems are of concern regardless of the duration of use of the stent. Irritation is of particular concern, however, when use of a stent is required over a long time period.

Another problem associated with ureteral stents is urine reflux and pain during urine voiding. On the initiation of voiding, the bladder wall muscles contract causing the pressure inside the bladder to increase. Because a typical ureteral stent holds the ureteral orifice open, increased bladder pressure during voiding is transmitted to the kidney through the stent, causing urine reflux and flank pain.

SUMMARY

Many factors thus should be considered when designing a ureteral stent. Such factors include the function to be performed by different parts of the stent, such as anchoring, maintenance of an open-flow condition, etc., and comfort. In particular, it is desirable to make a ureteral stent that is easy to insert, comfortable at all times, exhibits good coil recovery (the tendency of the stent ends to return to the originally-designed coiled state after having been straightened, for example, during insertion), remains anchored during normal bodily movements, provides for suitable flow of urine, is easily removable and avoids fracture during insertion, use and removal. The invention relates to various designs for a ureteral stent that facilitate many or all of the above goals by exhibiting varying characteristics along the length of the stent.

Ureteral stents according to embodiments of the invention include a tubular body defining a lumen and having (i) a distal kidney section to be placed in or near a patient's kidney, (ii) a proximal bladder section to be placed within the patient's bladder, and (iii) a ureter section between the distal and proximal sections to be placed within the patient's ureter.

According to a first aspect of the invention, the tubular body has a first material layer and a stiffening member that extends through at least a portion of a length of the tubular body. The stiffening member has a stiffness characteristic that varies along its length. This enables different portions of the stent to have different stiffness characteristics that preferably are optimized for the location of those portions within the human body.

According to some embodiments, the stiffening member has a first stiffness characteristic in the distal kidney section, and a second stiffness characteristic that is different from the first stiffness characteristic in one or both of the ureter section and the proximal bladder section. According to other embodiments, the stiffening member has a first stiffness characteristic in the proximal bladder section, and a second stiffness characteristic that is different from the first stiffness characteristic in one or both of the ureter section and the distal kidney section. According to other embodiments, the stiffening member has a first stiffness characteristic in the ureter section, and a second stiffness characteristic that is different from the first stiffness characteristic in one or both of the distal kidney section and the proximal bladder section. In some embodiments, the stiffening member has different stiffness characteristics in each of the distal kidney section, the ureter section, and the proximal bladder section.

According to some embodiments, the stiffening member includes at least a second material layer having a second stiffness that is different from a first stiffness of the first material layer. A shape of an interface between the first material layer and the second material layer may vary along the length of the tubular body in order to vary the stiffness characteristic along the length of the tubular body. A thickness (or cross-sectional area) of the first material layer and of the second material layer may vary along the length of the tubular body in order to vary the stiffness characteristic of the tubular body. Furthermore, a stiffness of the second material layer may vary along the length of the tubular body in order to vary the stiffness characteristic of the tubular body.

According to some embodiments, the stiffening member includes a plurality of additional material layers having different stiffness characteristics, with a number of the additional material layers varying along the length of the tubular body. This also results in the tubular body having different stiffness characteristics along different portions of its length.

According to some embodiments, the stiffening member includes at least one strand of material that is embedded within the first material layer. A thickness of the at least one strand of material may vary along the length of the tubular body so as to vary the stiffness characteristic of the tubular body along its length. According to some embodiments, a cross-sectional shape of the at least one strand of material varies along the length of the tubular body in order to vary the stiffness of the tubular body. According to other embodiments, a path of the at least one strand of material varies along the length of the tubular body so as to vary the stiffness characteristic of the tubular body along its length. According to some embodiments, a number of the strands of the material varies along the length of the tubular body in order to vary the stiffness characteristics of the tubular body along its length.

According to some embodiments, first and second strands having stiffness characteristics that differ from each other are embedded within the first material layer. The first strand can be located on a first side of the tubular body relative to a longitudinal axis of the tubular body. The second strand can be located on a second side of the tubular body relative to the longitudinal axis of the tubular body. Providing the first and second strands with different stiffness characteristics on first and second sides of the tubular body may cause the tubular body to have a preferential bending direction. Such a structure is particularly useful for forming the coiled ends of the stent.

According to another aspect of the invention, the tubular body includes at least a first material layer and a second material layer each of which extend through at least a portion of a length of the tubular body. The first material of the first material layer is different from the second material of the second material layer. In addition, at least one of a thickness, a cross-sectional shape and a longitudinal-sectional shape of one or both of the first and second material layers varies along the length of the tubular body. For example, the at least one of the thickness, cross-sectional shape and longitudinal-sectional shape of one or both of the first and second material layers can vary between the distal kidney section, the proximal bladder section, and the ureter section of the tubular body.

According to another aspect of the invention, the tubular body includes a first material layer and at least one strand of material embedded within the first material layer and that extends through at least a portion of a length of the tubular body. In addition, at least one of the following varies along the length of the tubular body: (a) a thickness of the at least one strand of material, (b) a cross-sectional shape of the at least one strand of material, (c) a path of the at least one strand of material, and (d) a number of the strands of the material. For example, the at least one of (a) the thickness of the at least one strand of material, (b) the cross-sectional shape of the at least one strand of material, (c) the path of the at least one strand of material, and (d) the number of the strands of the material, can vary between the distal kidney section, the proximal bladder section, and the ureter section of the tubular body.

BRIEF DESCRIPTION OF THE DRAWINGS

Various exemplary embodiments of ureteral stents according to aspects of the invention will be described in detail with reference to the following drawings in which.

DETAILED DESCRIPTION OF EMBODIMENTS

The invention relates to ureteral stents configured for improved patient comfort. In particular, the stents have different stiffness characteristics along the length of the stent. As a typical stent has a distal kidney section, a proximal bladder section and a ureter section between the distal and proximal sections, one or more of those sections are configured to have a stiffness characteristic that differs from the stiffness characteristic of one or both of the other sections. In addition, the stiffness characteristic can vary along all or part of a section, and also can vary in the region where two different sections join each other. In order to achieve the difference in stiffness characteristics, one or more stiffening members is/are included along at least a part of the length of the stent, and the stiffening member is configured to have a stiffness characteristic that varies along its length. According to some embodiments, the stiffening member is a material layer that differs in stiffness characteristic compared to a first material layer that forms a majority of the stent. Furthermore, the stiffness characteristic of the stent can be varied by varying at least one of a thickness, a cross-sectional shape and a longitudinal-sectional shape of one or both of the first and second material layers along all or part of the length of the stent. According to some embodiments, the stiffening member is one or more strands of material embedded within the first material layer that forms the majority of the stent. In order to vary the stiffness of the stent along its length, at least one of the following varies along the length of the tubular body: (a) a thickness of the one or more strands of material, (b) a cross-sectional shape of the one or more strands of material, (c) a path of the one or more strands of material, and (d) a number of the strands of material.

Figure 1:
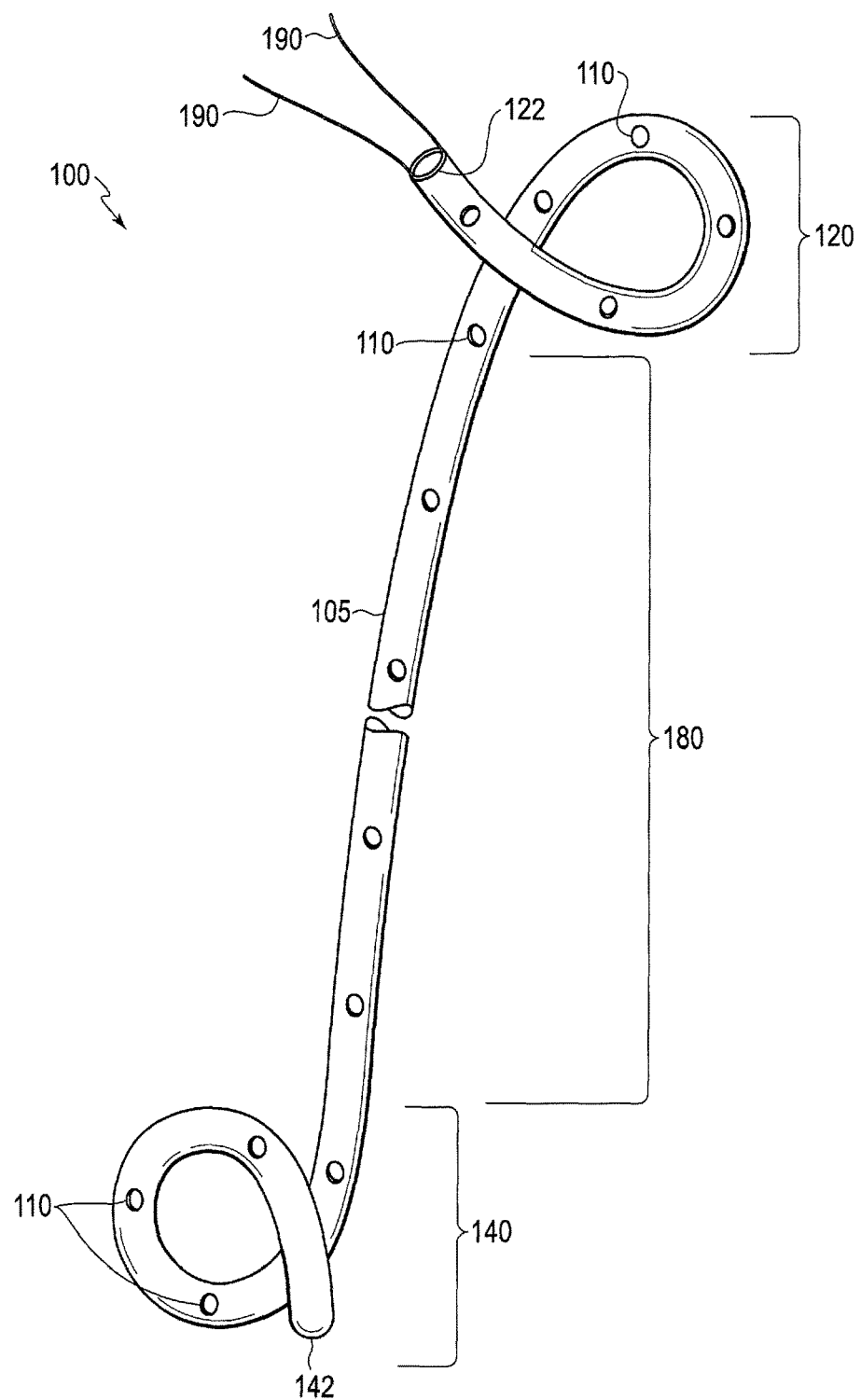
FIG. 1 shows a ureteral stent according to embodiments of the invention.

FIG. 1 shows a ureteral stent according to one embodiment of the invention. The stent 100 is a tubular, catheter-like body 105 having an internal lumen 106 (not shown in FIG. 1) extending from the distal end 142 to the proximal end 122. There can be a distal-most opening at the distal end 142, or the distal end 142 could be a rounded, closed end. Similarly, the proximal end 122 could have a proximal-most opening or the proximal end 122 could be rounded and closed. The tubular body 105 includes openings 110 along its length through which liquid such as urine may flow through the stent 100. The stent 100 essentially has three sections: (1) distal kidney section 140 that will be located within the kidney during use, (2) proximal bladder section 120 that will be located within the bladder during use, and (3) ureter section 180 that will be located within the ureter during use and which is disposed between the distal kidney section 140 and the proximal bladder section 120. In addition, strings 190 may be provided at the proximal end 122 of the proximal bladder section 120 for use in removing the stent 100 from the patient.

Figure 2:
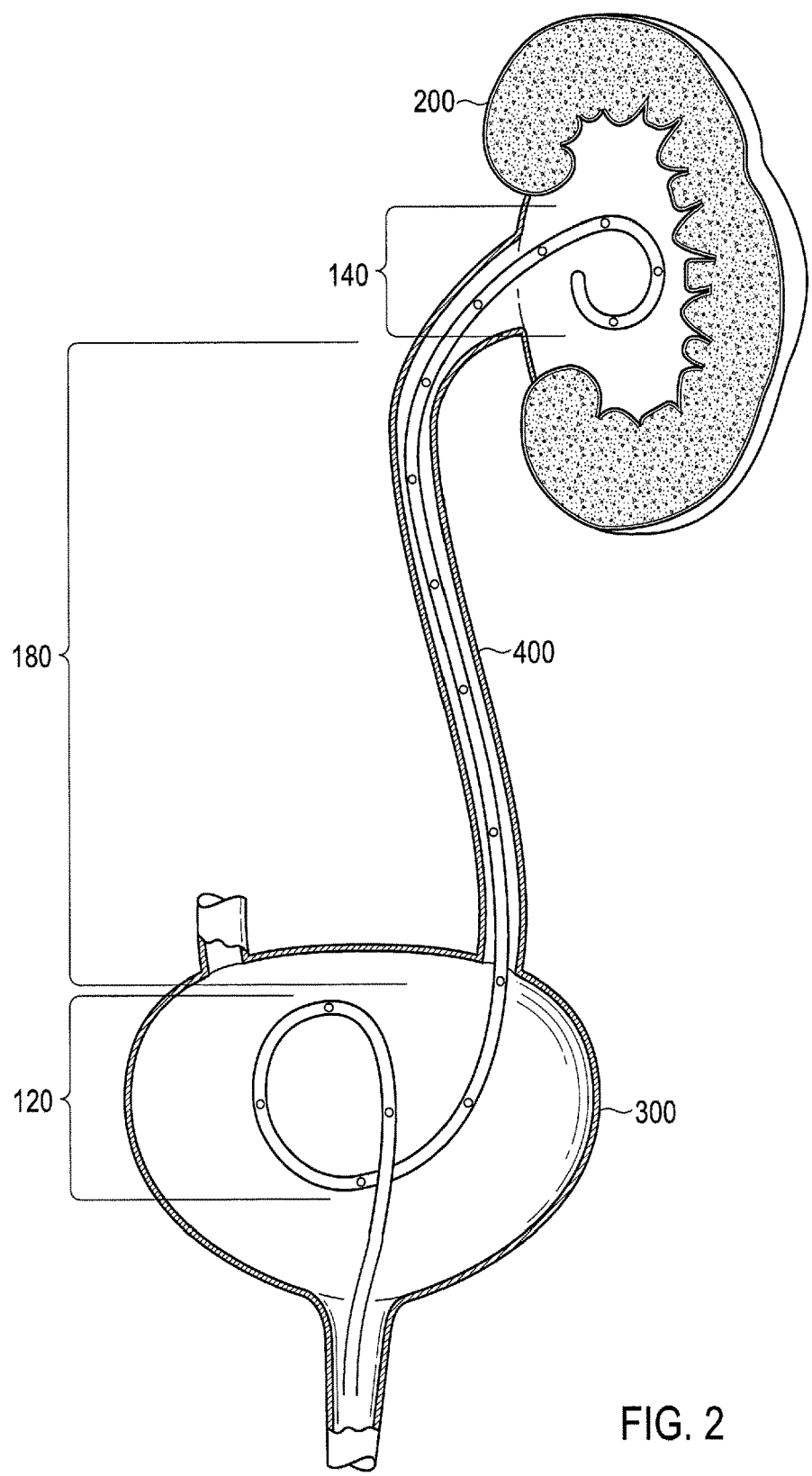
FIG. 2 shows a ureteral stent disposed within a patient's kidney, ureter and bladder.

FIG. 2 shows one manner in which the stent 100 can be disposed within the human body. Distal kidney section 140 will be disposed within the patient's kidney 200, proximal bladder section 120 will be disposed within the patient's bladder 300, and ureter section 180 will be disposed within the patient's ureter 400. As noted above, in order to increase patient comfort, it is desirable to configure the different sections of the stent to have different stiffness characteristics. For example, it can be desirable to have the distal kidney section 140 be the stiffest section of the stent, the proximal bladder section 120 be the least stiff (softest) section of the stent, and the ureter section 180 be a transition zone from stiffest (near the distal kidney section 140) to the least stiff (near the proximal bladder section 120). The distal kidney section 140 can be designed to resist stent migration by making it stiffer and providing a higher coil strength than other portions of the stent. The proximal bladder section 120 can be designed to focus on comfort, for example, by making it softer than other portions of the stent. The ureter section 180 can be designed to improve comfort during insertion, however, this region is not as critical as the distal kidney section 140 and the proximal bladder section 120. Different waveform interlayers (see FIGS. 3A-4F) and/or interstitching structure (see FIGS. 5A-7C) could be designed along the length of stent 100 so that the stent 100 has a variable stiffness along its length to meet a favorable stress concentration profile with comfort stent features, specifically targeted at the different regions.

FIGS. 3A-3H relate to embodiments in which one or more stiffening members in the form of a material layer is/are incorporated into the stent. Each of FIGS. 3A-3H is a cross-sectional view taken through the stent in a direction orthogonal to the longitudinal axis of the stent. Thus, in each of FIGS. 3A-3H, the internal lumen 106 is present in the cross-sectional view. The shape of the interface between two layers can take many forms. For example, the interface shape can be polygonal (a triangle, a quadrilateral, a pentagon, a hexagon, etc.), conic (a circle, an ellipse, a parabola, a hyperbola, etc.), or the interface can have different symmetries including but not limited to reflection, rotational, translational, roto-reflection, helical, non-isometric, scale and fractals.

Figure 3A:
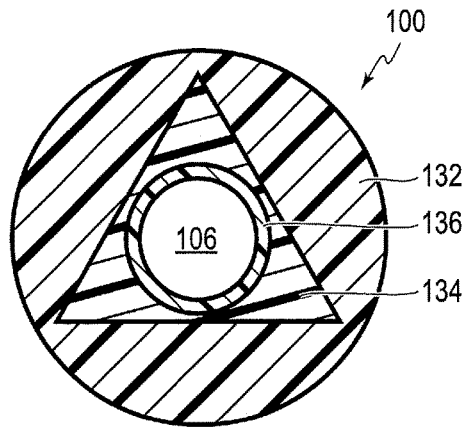
FIGS. 3A-3H are cross-sectional views of stents showing different material layers and different shapes of the interface between those material layers.

FIG. 3A shows an embodiment in which three material layers 132, 134 and 136 are present in at least part of the stent. The first material layer 132 defines the outer surface of the stent 100. The first material layer can be, for example, various polyurethanes, polyolefins, silicone, and/or proprietary polymers (such as Tecoflex™, Tecophillic™, Carbothan™, Tecothane™, Pellethan™, C-Flex™, Percuflex™, Silitek™, etc.). The second material layer 134 is made from a material having a stiffness characteristic different from the stiffness characteristic of the first material layer 132. The second material layer 134 can be, for example, various polyurethanes, polyolefins, silicone, and/or proprietary polymers (such as Tecoflex™, Tecophillic™, Carbothan™, Tecothane™, Pellethan™, C-Flex™, Percuflex™, Silitek™, etc.). As can be seen from FIG. 3A, the interface between the first material layer 132 and the second material layer 134 has a triangular shape in cross-section. A third material layer 136 is the innermost layer such that it forms a surface of the lumen 106. The third material layer 136 is made from a material different from at least the second material layer 134 (and in some embodiments different from both the first material layer 132 and the second material layer 134). The third material layer 136 also can be selected from, for example, various polyurethanes, polyolefins, silicone, and/or proprietary polymers (such as Tecoflex™, Tecophillic™, Carbothan™, Tecothane™, Pellethan™, C-Flex™, Percuflex™, Silitek™, etc.). As can be seen from FIG. 3A, the interface between the second material layer 134 and the third material layer 136 is circular. By varying the shape of the interfaces, as well as the cross-sectional area of each material layer along a length of the tubular body 105 of the stent 100, the stiffness of the stent can vary along the length of the stent.

Figure 3B:
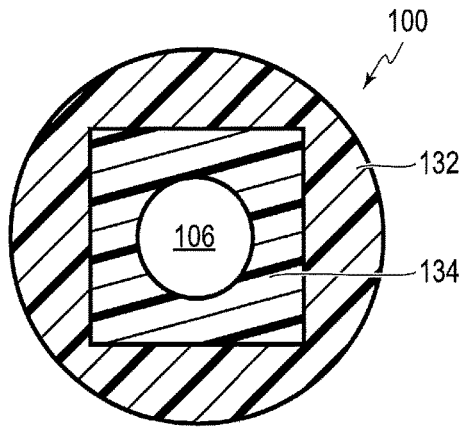

FIG. 3B shows an embodiment in which only two material layers are used. The first material layer 132 forms the outer surface of the stent 100. The second material layer 134 forms the lumen 106 of the stent 100. The shape of the interface between the first material layer 132 and the second material layer 134 is square. As with FIG. 3A, different materials are used for each of layers 132 and 134, the different materials having different stiffness characteristics. Layers 132 and 134 can be selected from the same materials described above in connection with FIG. 3A.

Figure 3C:
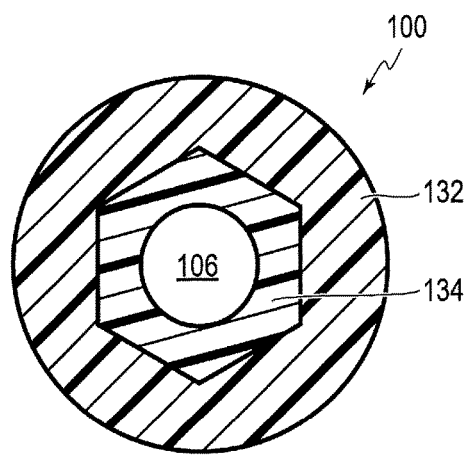

FIG. 3C shows an embodiment in which only two material layers are used. The first material layer 132 forms the outer surface of the stent 100. The second material layer 134 forms the lumen 106 of the stent 100. The shape of the interface between the first material layer 132 and the second material layer 134 is hexagonal. As with FIG. 3A, different materials are used for each of layers 132 and 134, the different materials having different stiffness characteristics. Layers 132 and 134 can be selected from the same materials described above in connection with FIG. 3A.

Figure 3D:
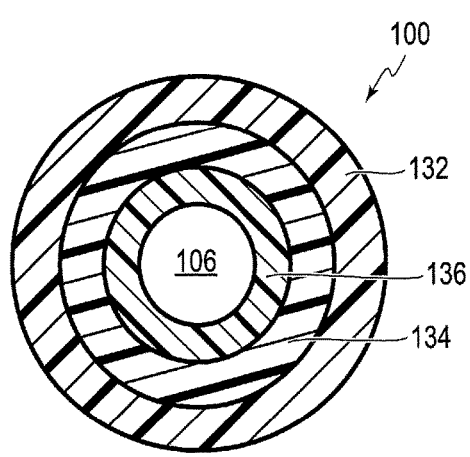

FIG. 3D shows an embodiment in which three material layers are used. The first material layer 132 forms the outer surface of the stent 100. The second material layer 134 is located radial inward of the first material layer 132. A third material layer 136 forms the lumen 106 of the stent 100. The shape of the interface between the first material layer 132 and the second material layer 134 is round. The shape of the interface between the second material layer 134 and the third material layer 136 also is round. As with FIG. 3A, different materials are used for each of layers 132, 134 and 136, the different materials having different stiffness characteristics. Layers 132, 134 and 136 can be selected from the same materials described above in connection with FIG. 3A.

Figure 3E:
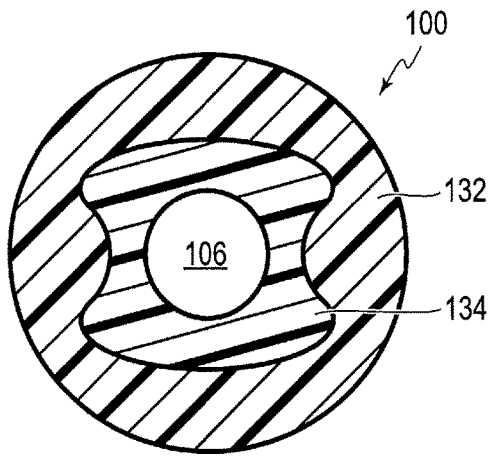

FIG. 3E shows an embodiment in which only two material layers are used. The first material layer 132 forms the outer surface of the stent 100. The second material layer 134 forms the lumen 106 of the stent 100. The shape of the interface between the first material layer 132 and the second material layer 134 is parabolic. As with FIG. 3A, different materials are used for each of layers 132 and 134, the different materials having different stiffness characteristics. Layers 132 and 134 can be selected from the same materials described above in connection with FIG. 3A.

Figure 3F:
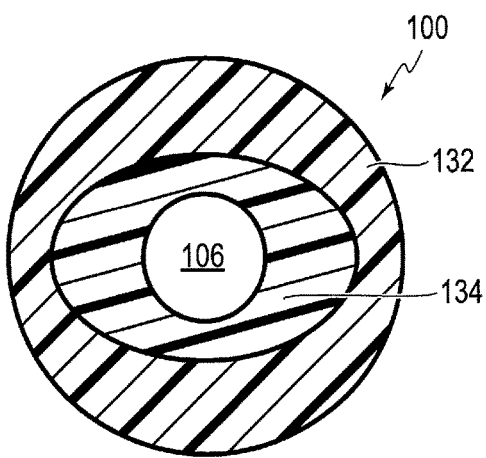

FIG. 3F shows an embodiment in which only two material layers are used. The first material layer 132 forms the outer surface of the stent 100. The second material layer 134 forms the lumen 106 of the stent 100. The shape of the interface between the first material layer 132 and the second material layer 134 is elliptical. As with FIG. 3A, different materials are used for each of layers 132 and 134, the different materials having different stiffness characteristics. Layers 132 and 134 can be selected from the same materials described above in connection with FIG. 3A.

Figure 3G:
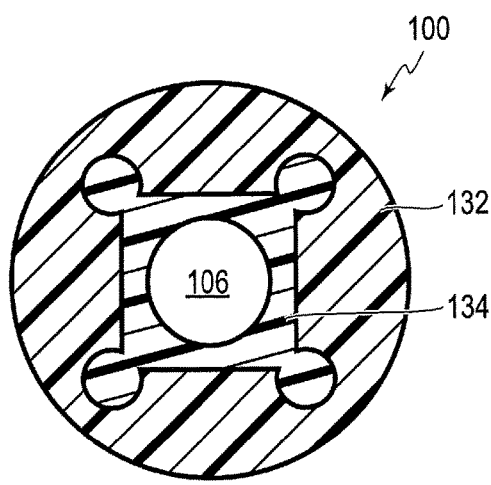
Figure 3H:
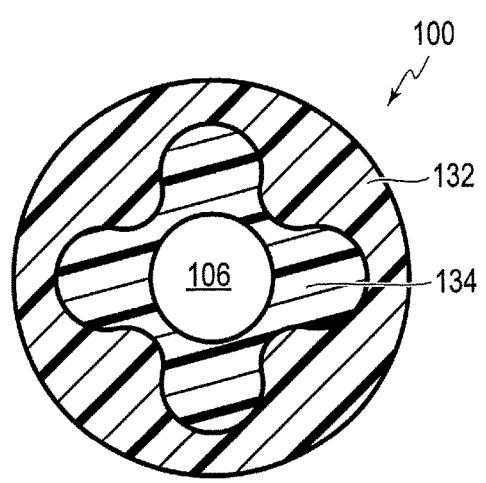

FIGS. 3G and 3H show embodiments in which only two material layers are used. The first material layer 132 forms the outer surface of the stent 100. The second material layer 134 forms the lumen 106 of the stent 100. The shape of the interface between the first material layer 132 and the second material layer 134 is irregular but symmetrical with respect to two perpendicular axes that each are perpendicular to the longitudinal axis of the stent. As with FIG. 3A, different materials are used for each of layers 132 and 134, the different materials having different stiffness characteristics. Layers 132 and 134 can be selected from the same materials described above in connection with FIG. 3A.

The different cross-sectional configurations shown in FIGS. 3A-3H can vary along the length of the stent. For example, referring to FIG. 3A, layer 136 can be stiffer than layers 132 and 134, and further, layer 134 can be stiffer than layer 132. The three layers 132, 134 and 136 can be present in the distal kidney section 140 so that the distal kidney section 140 is relatively stiff. Only layers 132 and 134 may be present in the ureter section 180 so that the ureter section 180 is less stiff than the distal kidney section 140. Furthermore, the proximal bladder section 120 could be the same as the ureter section (having layers 132 and 134) or the proximal bladder section 120 may have only the material layer 132 so as to be less stiff than both the distal kidney section 140 and the ureter section 180. Furthermore, the thickness of a layer (for example, layer 136) could gradually decrease as one moves proximally from the distal end of the ureter section 180 (or even from within the proximal end of the distal kidney section 140) until the layer 136 terminates either within the ureter section 180 or within the distal end of the proximal bladder section 140. Also, two or more of the different cross-sectional structures shown in FIGS. 3A-3H could be present within a single stent 100 at different longitudinal positions along the length of the stent 100.

Figure 4A:
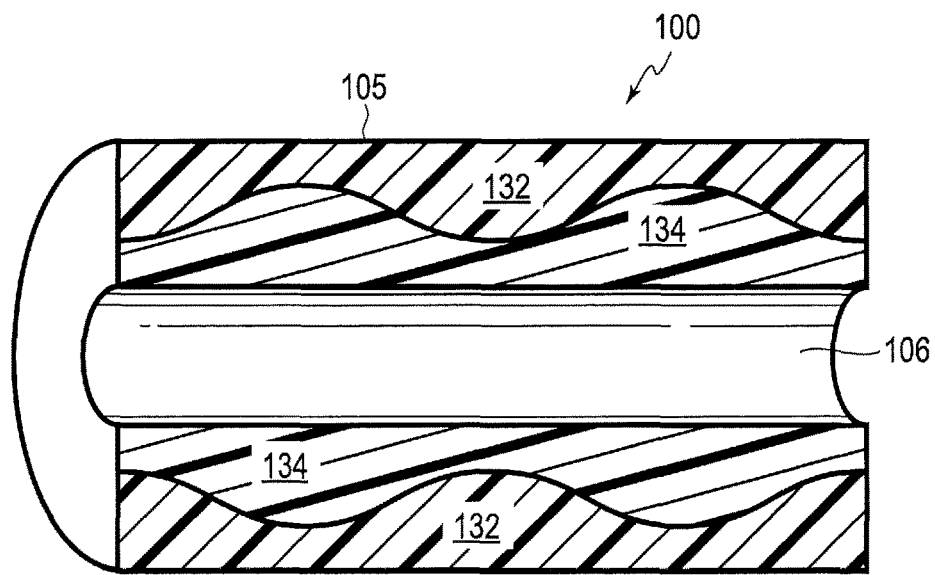
FIGS. 4A-4F are cross-sectional views of multi-material-layer stents taken through a plane that is parallel to the longitudinal axis of the stent.
Figure 4B:
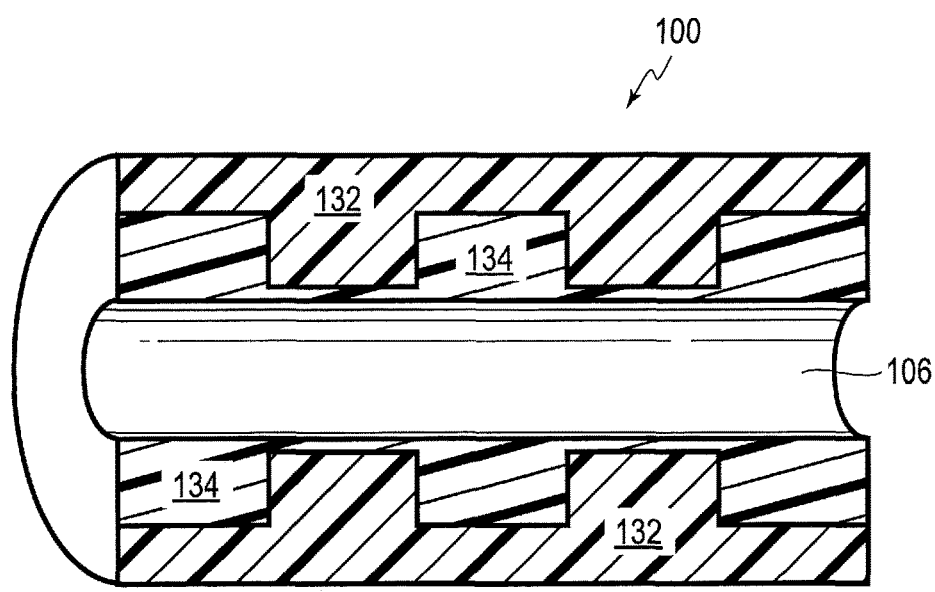
Figure 4C:
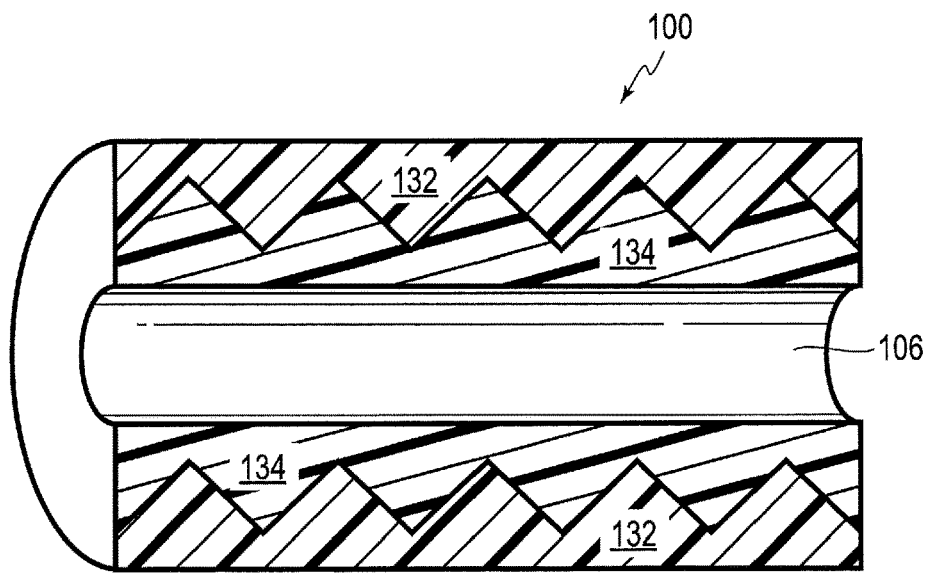
Figure 4D:
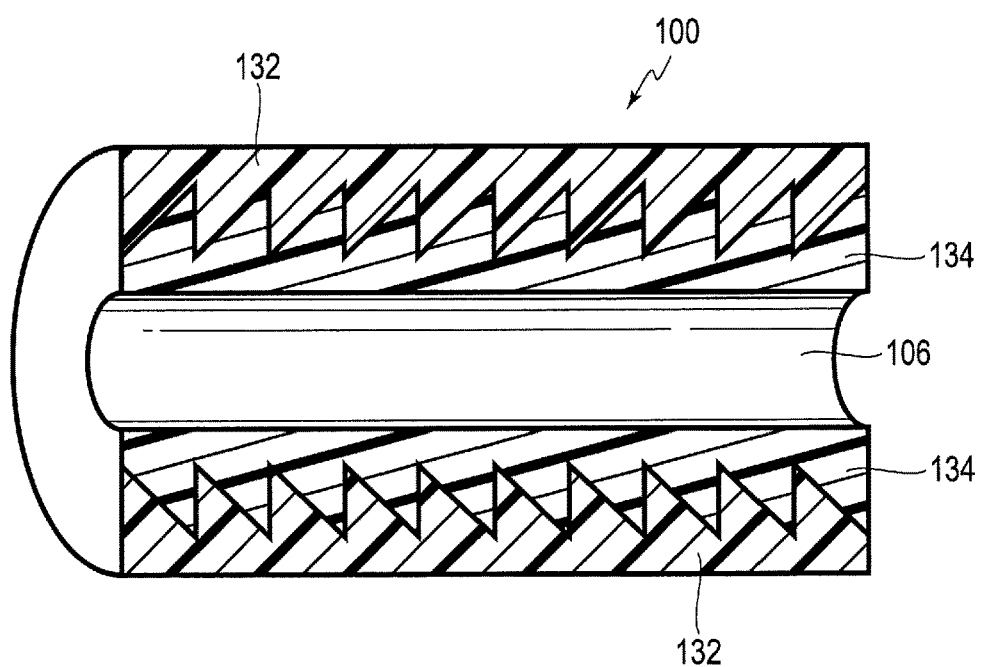
Figure 4E:
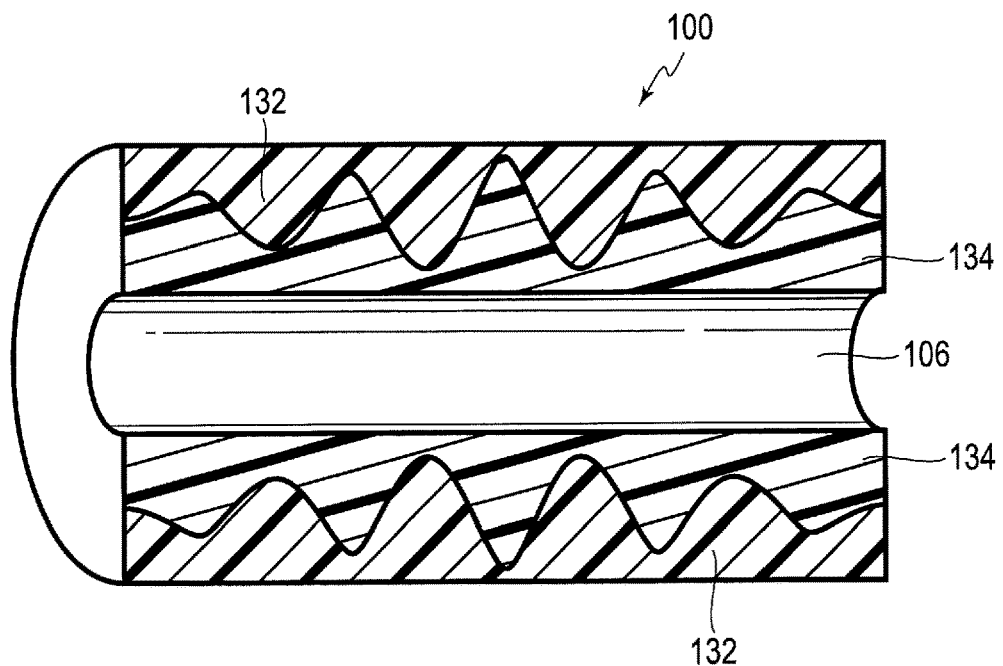
Figure 4F:
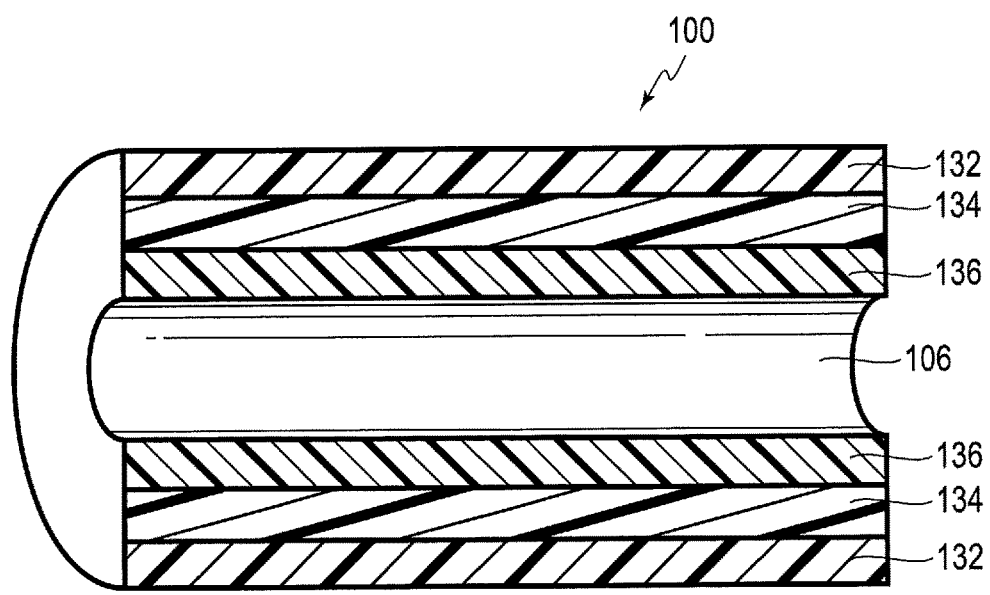

FIGS. 4A-4F are cross-sectional views of multi-material-layer stents taken through a plane that is parallel to the longitudinal axis of the stent. As shown in FIGS. 4A-4F, the interface between two layers can vary like a wave when viewed in the longitudinal direction of the stent. The wave form between two layers in the longitudinal direction includes but is not limited to sine waves (FIG. 4A), square waves (FIG. 4B), triangle waves (FIG. 4C), saw tooth waves (FIG. 4D), Fourier Transform waves (FIG. 4E), longitudinally straight interfaces (FIG. 4F). The different waveforms shown in FIGS. 4A-4F could be used along part of the length of the stent to provide a stiffness characteristic associated with that waveform to the part of the length of the stent at which the waveform is provided. Different waveforms shown in FIGS. 4A-4F also could be present within a single stent 100 at different longitudinal positions along the length of the stent 100. The longitudinal profiles of stent 100 may vary along the length of stent 100, and different cross-sectional shapes may be utilized along the length of stent 100. Various waveform profiles may be combined to form a single stent combination design.

A comfort stent profile can be created using different waveforms and interstitching to better match the elastic modulus of the urinary tract system. Typical modulus of elasticity (E) for soft tissue is between about 0.3 kPa and 3 kPA. A design concept for stent 100 may be best matched for comfort through a matching with the elastic modulus of the tissues along the insertion path as well as the inserted position.

It may be more desirable to have a cross-sectional profile that would result in a configuration which was relatively harder to bend in certain sections along the length of stent 100. For example, the cross sectional profiles of FIG. 3A or 3G may result in a stent which was relatively harder to bend. It may also be desirable to have a cross-sectional profile that would result in a configuration which was relatively softer, or easier to bend, in certain sections along the length of the stent 100. For example, the cross sectional profiles of FIG. 3D or 3F may result in a stent which was relatively softer, or easier to bend. It may also be desirable to have a cross sectional profile that was somewhere in between hard and soft. For example, the cross sectional profiles of FIGS. 3B and 3C may result in a stent which was somewhere in between hard and soft in terms of bending rigidity.

It is contemplated that one might desire to have a more rigid stent at the insertion end, or in the distal kidney section 140. One might desire to have a less rigid stent at the proximal bladder section 120. One might desire to have a stiffness somewhere in between for the ureter section 180. In particular at the ureteropelvic junction (UPJ), approximately where the distal kidney section 140 and the ureter section 180 meet, and at the ureterovesical junction (UVJ), approximately where the ureter section 180 and the proximal bladder section 120 meet, one might desire a cross sectional profile that would result in the most comfort as this is an area of irritation in more traditional stents.

Any of the transverse cross-section configurations shown in FIGS. 3A-3H can be combined with any of the longitudinal cross-section configurations shown in FIGS. 4A-4F.

FIGS. 5A-5F relate to embodiments in which one or more stiffening members in the form of a strand of material layer is/are incorporated into the stent. A thickness of the at least one strand of material may vary along the length of the tubular body so as to vary the stiffness characteristic of the tubular body along its length. According to some embodiments, a cross-sectional shape of the at least one strand of material varies along the length of the tubular body in order to vary the stiffness of the tubular body. According to other embodiments, a path of the at least one strand of material varies along the length of the tubular body so as to vary the stiffness characteristic of the tubular body along its length. According to some embodiments, a number of the strands of the material varies along the length of the tubular body in order to vary the stiffness characteristics of the tubular body along its length. Each of FIGS. 5A-5F is a cross-sectional view taken through the stent in a direction orthogonal to the longitudinal axis of the stent. Thus, in each of FIGS. 5A-5F, the internal lumen 106 is present in the cross-sectional view. The number of strands present varies in each of FIGS. 5A-5F.

Figure 5A:
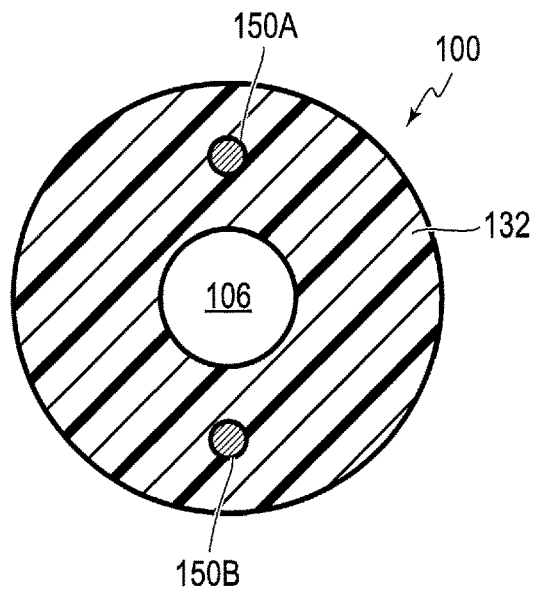
FIGS. 5A-F are cross-sectional views of stents showing different numbers of strands used as a stiffening member, the cross-section taken through a plane that is orthogonal to the longitudinal axis of the stent.

In FIG. 5A, two strands 150A and 150B are present. Strands 150A and 150B are disposed at intervals of 180 degrees around the circumference of the stent, although other arrangements are possible and contemplated herein. The tubular body portion of the stent 100 can be made from a single material layer, such as the material layer 132 described above, or it can have multiple material layers in all or only parts of the length of the stent as described above in connection with FIGS. 3A-3H. Strands 150A and 150B are made of, for example, materials similar to the materials described above in connection with layers 132, 134 and 136. The strands 150A and 150B could be identical to each other or could have different stiffnesses, for example, by being made from different materials or by having different diameters or cross-sectional shapes. By making the strands 150A and 150B on opposite sides of the longitudinal axis have different stiffnesses, the portion of the stent having the strands will preferentially bend in one direction.

It is well known that during stent insertion, soft stent materials such as silicone especially when in combination with a complex tortuous insertion path may have some degree of insertion difficulty due to potential buckling as well as potential high surface friction. The waveform interlayer and interstitching stent design concept of the present invention could be used for overcoming the issue of insertion for soft stent materials through materials selection, stent stress design at either dynamic load condition or static load condition (compression and tension) by varying both the cross-sectional profile and longitudinal profile using different materials for the different sections within the cross sectional or longitudinal profiles. By way of example, it may be desired for the material durometer to be harder, in the range of 10 to 50 Shore A, at the distal kidney section 140. Further, it may be desired for the material durometer to be softer, in the range of 50 to 90 Shore A, at the proximal bladder section 120. In the ureter section 180, the material durometer may be somewhere in between the material durometer of the distal kidney section 140 and the proximal bladder section 120.

It is contemplated that a stent designer would desire a ureteral stent that provided for a combination of increased comfort as well as resistance to buckling during insertion. Euler's formula for buckling, $$F = \frac{\pi^2 EI}{(KL)^2},$$

where F is the maximum or critical force, E is Young's Modulus, I is the area moment of inertia, K is the column effective length factor, and L is the unsupported column length, could be a good guideline for critical load design. The critical force which would cause buckling can be modified with a changing modulus of elasticity, changing surface friction coefficient, changing moment of inertia, changing unsupported column length, and changing column effective length factor. Also, the strands can be positioned in only a portion of the length of the stent so that the portion has a stiffness characteristic associated with the strands. For example, if the strands 150A and 150B are stiffer than the material 132 making up the remainder of the stent, the strands can be disposed only in the distal kidney section 140 so that the distal kidney section 140 is stiffer than the ureter section 180 and the proximal bladder section 120 of the stent. In addition, the number of strands within a cross-section of the stent can diminish as one moves proximally along the length of the stent so that the stent becomes less stiff as one moves proximally. For example, two strands can be present in the distal kidney section 140, one strand can be present in all or at least the distal part of the ureter section 180, and the proximal bladder section 120 can be provided with no strand.

Other strand arrangements are possible. Some alternative arrangements are shown in connection with FIGS. 5B-5F.

Figure 5B:
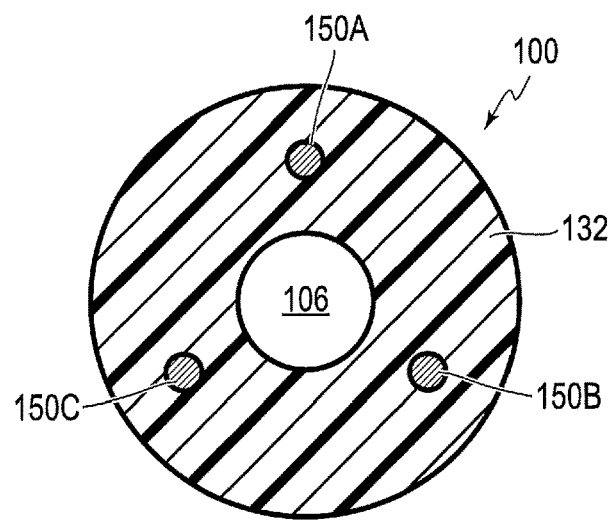

In FIG. 5B, three strands 150A, 150B and 150C are present. The strands 150A-150C are disposed at intervals of 120 degrees around the circumference of the stent, although other arrangements are possible and contemplated herein.

Figure 5C:
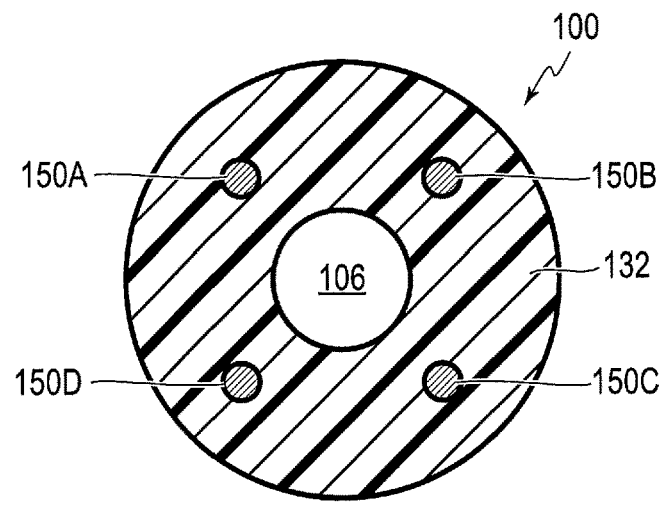

In FIG. 5C, four strands 150A, 150B, 150C and 150D are present. The strands 150A-150D are disposed at intervals of 90 degrees around the circumference of the stent, although other arrangements are possible and contemplated herein.

Figure 5D:
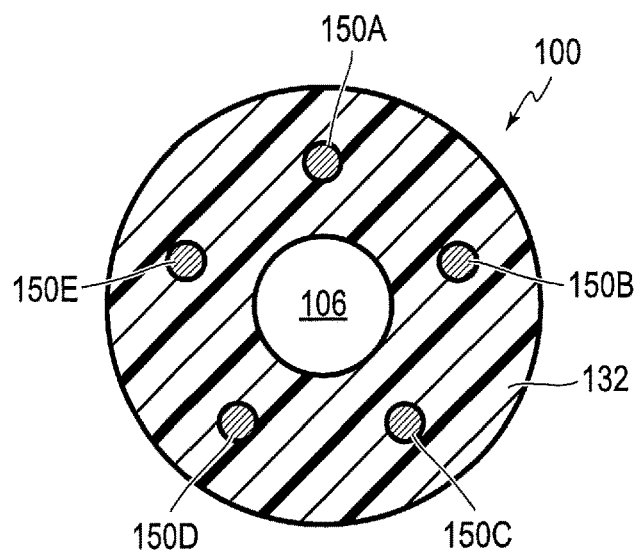

In FIG. 5D, five strands 150A, 150B, 150C, 150D and 150E are present. The strands 150A-150E are disposed at intervals of 72 degrees around the circumference of the stent, although other arrangements are possible and contemplated herein.

Figure 5E:
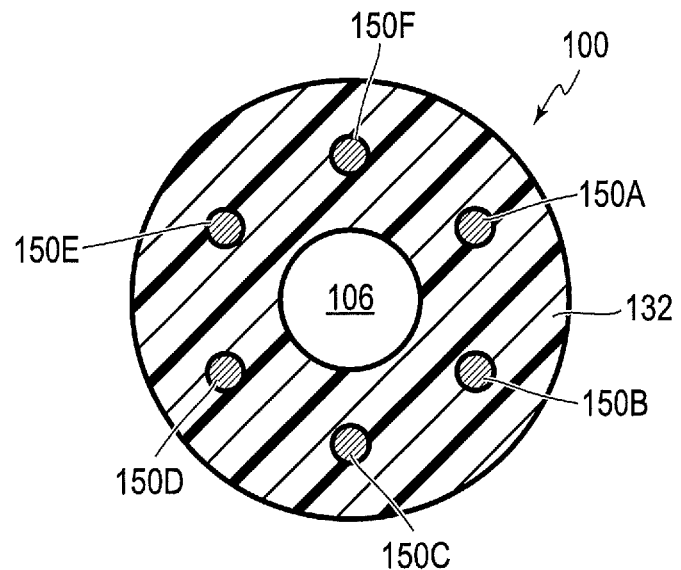

In FIG. 5E, six strands 150A, 150B, 150C, 150D, 150E and 150F are present. The strands 150A-150F are disposed at intervals of 60 degrees around the circumference of the stent, although other arrangements are possible and contemplated herein.

Figure 5F:
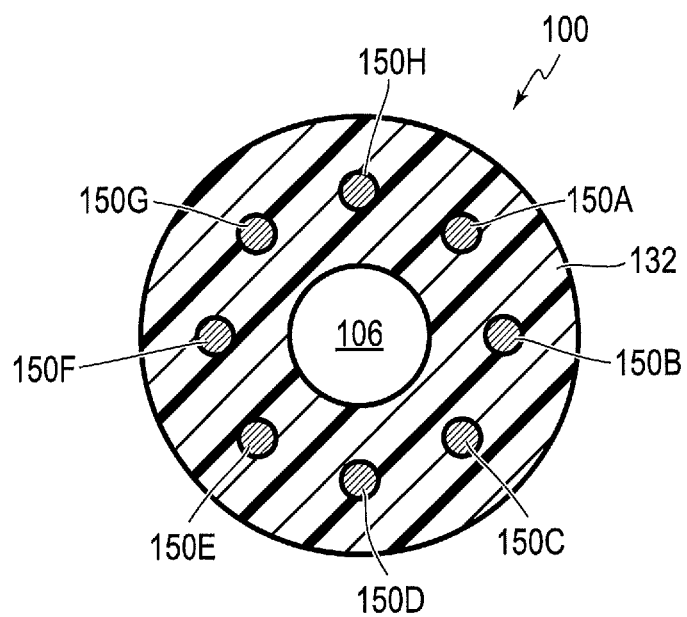

In FIG. 5F, eight strands 150A, 150B, 150C, 150D, 150E, 150F, 150G and 150H are present. The strands 150A-150H are disposed at intervals of 45 degrees around the circumference of the stent, although other arrangements are possible and contemplated herein.

Figure 6A:
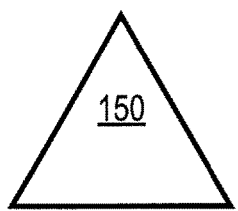
FIGS. 6A-6L show cross-sectional shapes of strands that may be used.
Figure 6B:
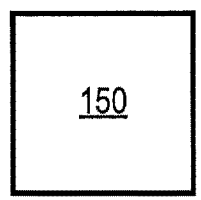
Figure 6C:
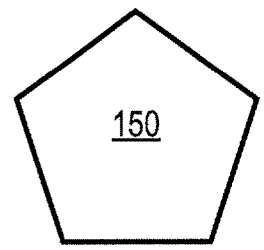
Figure 6D:
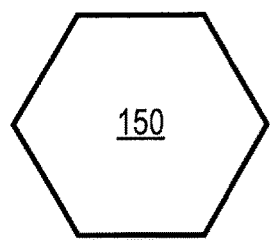
Figure 6E:
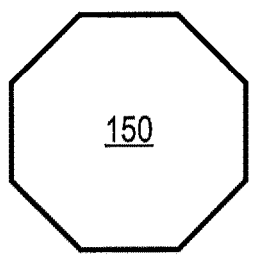
Figure 6F:
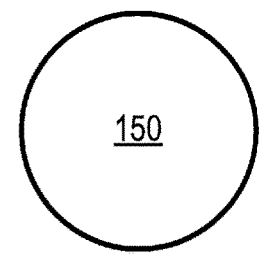
Figure 6G:
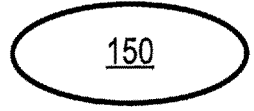
Figure 6H:
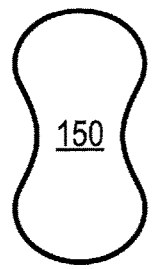
Figure 6I:
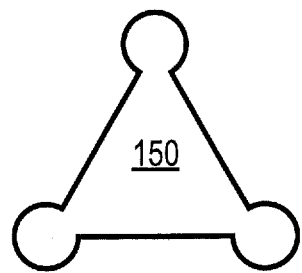
Figure 6J:
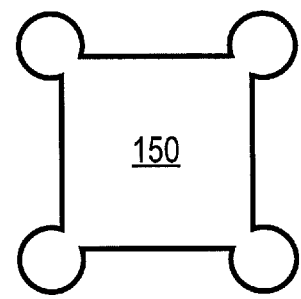
Figure 6K:
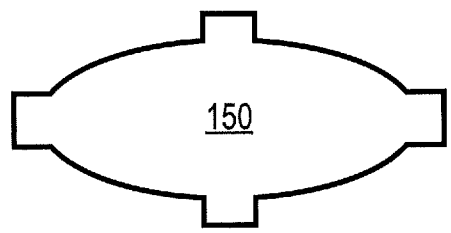
Figure 6L:
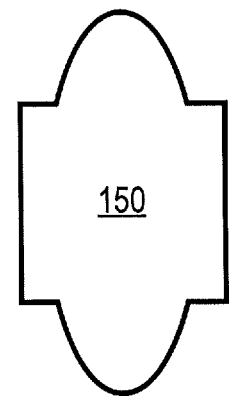

FIGS. 6A-6L show cross-sectional shapes of strands 150 that may be used. The strands 150 can have various shapes in cross-section taken through a plane that is orthogonal to the longitudinal axis of the stent (and of the strand). The cross-sectional shape can be polygonal (triangle, quadrilateral, pentagon, hexagon, etc.), conic (circle, ellipse, parabola, hyperbola, etc.), or the strand cross-section can have different symmetries including but not limited to reflection, rotational, translational, roto-reflection, helical, non-isometric, scale and fractals. In FIG. 6A, the cross-sectional shape is a triangle. In FIG. 6B, the cross-sectional shape is a square. In FIG. 6C, the cross-sectional shape is a pentagon. In FIG. 6D, the cross-sectional shape is a hexagon. In FIG. 6E, the cross-sectional shape is an octagon. In FIG. 6F, the cross-sectional shape is a circle. In FIG. 6G, the cross-sectional shape is an ellipse. In FIG. 6H, the cross-sectional shape is a parabola. In FIGS. 6I, 6J, 6K and 6L, the cross-sectional shape is formed by combining polygons with conic sections.

Figure 7A:
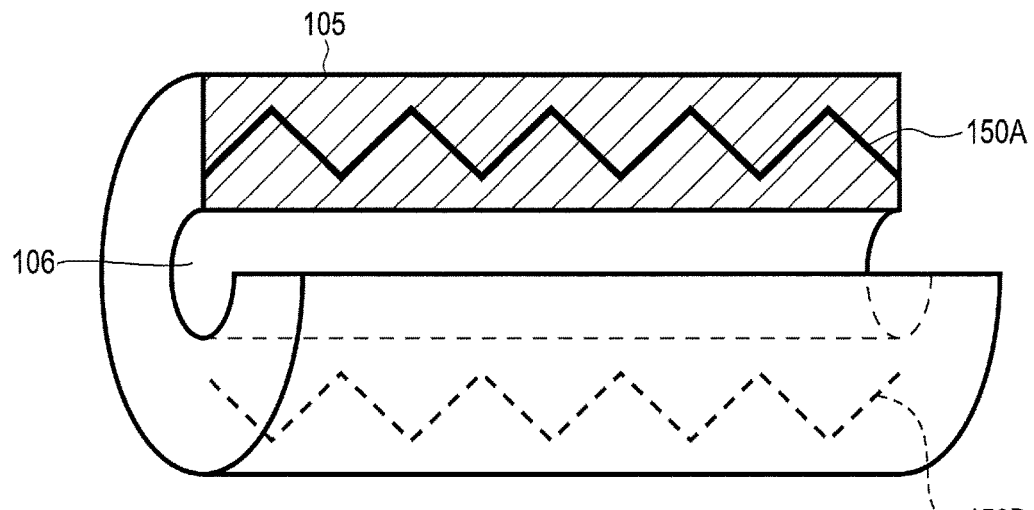
FIGS. 7A-7C are cross-sectional views, taken through a plane that is parallel to the longitudinal axis of the stent, of stents having one or more strands of material therein.
Figure 7B:
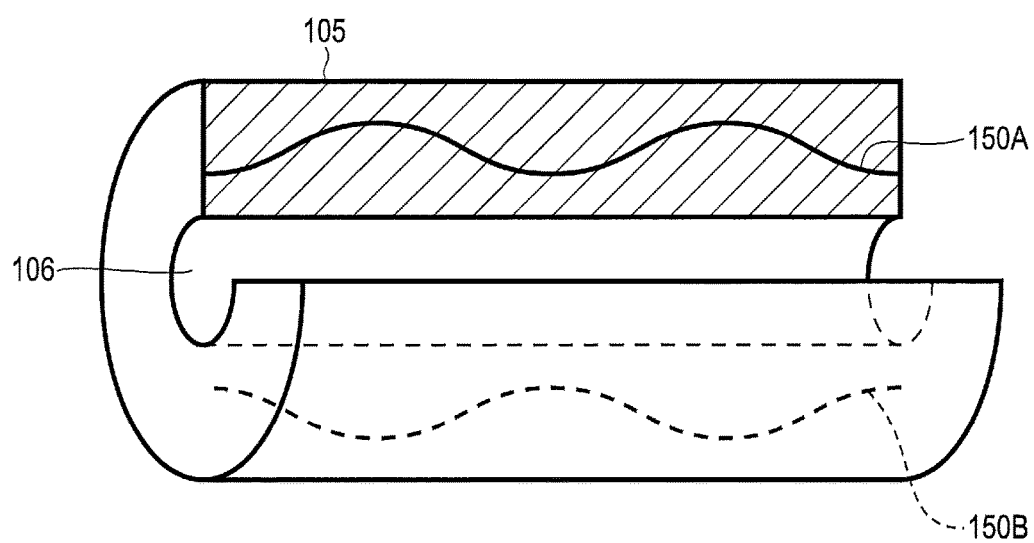
Figure 7C:
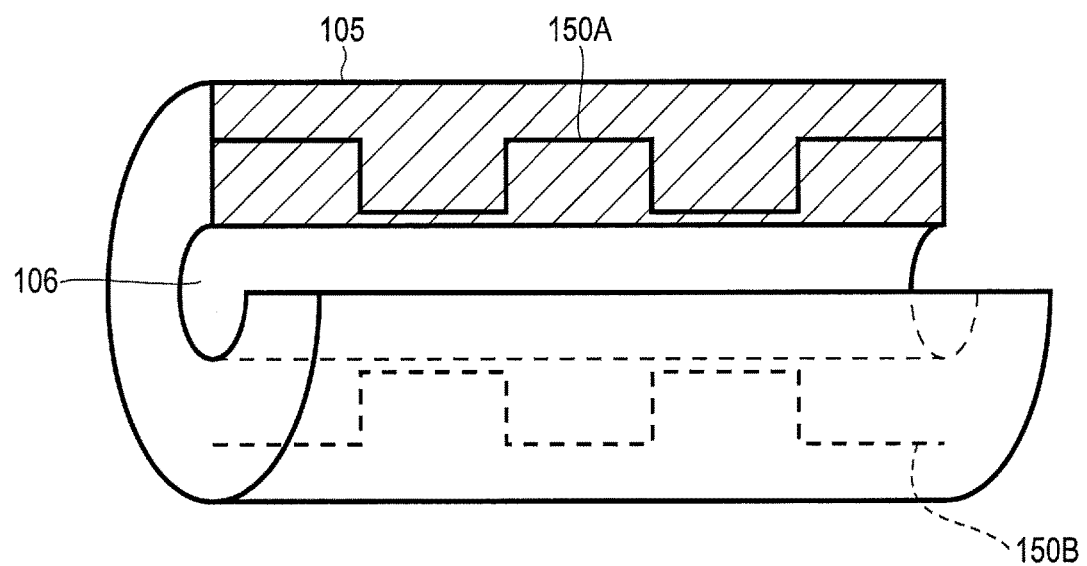

FIGS. 7A-7C are cross-sectional views, taken through a plane that is parallel to the longitudinal axis of the stent, of stents having one or more strands of material therein. As shown in FIGS. 7A-7C, the radial position of the strand (distance of the strand from the central, longitudinal axis of the stent) can vary like a wave when viewed in the longitudinal direction of the stent. The wave form of the strand(s) in the longitudinal direction includes but is not limited to triangle waves (FIG. 7A), sine waves (FIG. 7B) and square waves (FIG. 7C), although other waveforms such as waveforms shown in FIGS. 4D-4F are contemplated herein. The broken line waveform for strand 150B in FIGS. 7A-7C means that the strand 150B can be different in stiffness from strand 150A. Such a structure gives the portion of the stent having the strands 150A and 150B a preferential bending direction as discussed earlier. The different waveforms shown in FIGS. 7A-7C could be used along part of the length of the stent to provide a stiffness characteristic associated with that waveform to the part of the length of the stent at which the waveform is provided. Different waveforms shown in FIGS. 7A-7C also could be present within a single stent 100 at different longitudinal positions along the length of the stent 100. Adjusting the waveform interlayers and interstitching design choices along the length of the ureteral stent 100 may provide a designer with more comfort feature flexibility in one stent design.

Any of the transverse cross-section configurations shown in FIGS. 5A-5F can be combined with any of the transverse strand cross-sections shown in FIGS. 6A-6L, and any of those combinations can be combined with any of the longitudinal cross-section configurations shown in FIGS. 7A-7C.

In addition, any of the embodiments using multiple material layers can be combined with any of the embodiments using one or more strands.

By providing the various configurations described above in different sections of the stent, each stent section can be configured to have desired characteristics in terms of stiffness. This improves the comfort level that can be achieved with a ureteral stent.

Materials selection as well as stent structure will be critical for comfort stent design at the distal kidney section 140 and at the proximal bladder section 120. Ureter section 180 may be less critical as far as the exact waveform interlayer or interstitching selected. Choice of waveform interlayers and interstitching design concepts provides options for the comfort stent designer.

Stents having the structures described above preferably are made by co-extrusion processes. Co-extrusion processes are continuous processes that are more robust and easier to modify than batch-type processes.

The illustrated exemplary embodiments are intended to be illustrative and not limiting. Various changes may be made without departing from the spirit and scope of the invention.

What is claimed is:

1. A ureteral stent comprising:
a tubular body defining a lumen and having: (i) a kidney section to be placed in or near a patient's kidney, (ii) a bladder section to be placed within the patient's bladder, and (iii) a ureter section between the kidney and bladder sections to be placed within the patient's ureter, the tubular body having:
a first material layer; and
a stiffening member that extends through at least a portion of a length of the tubular body, the stiffening member having a stiffness characteristic that varies along its length and including at least one strand that is embedded within the first material layer, a cross-sectional shape of the at least one strand varying along the length of the tubular body.

2. The ureteral stent according to claim 1, wherein the cross-sectional shape of the at least one strand varies between the kidney section, the bladder section, and the ureter section of the tubular body.

3. The ureteral stent of claim 1, further comprising:
a second material layer which extends through at least a portion of a length of the tubular body.

4. The ureteral stent of claim 3, wherein the at least one strand includes a first strand and a second strand having stiffness characteristics that differ from each other.

5. The ureteral stent of claim 3, wherein at least one of a thickness, a cross-sectional shape and a longitudinal-sectional shape of one or both of the first and second material layers varies along the length of the tubular body.

6. The ureteral stent of claim 1, wherein a material durometer of the bladder section is in a range of 50 to 90 Shore A.

7. The ureteral stent of claim 1, wherein the stiffness characteristic varies in a region where two of the kidney section, the bladder section, and the ureter section join each other.

8. The ureteral stent of claim 2, wherein the stiffening member is most stiff in the kidney section, is least stiff in the bladder section, and has an intermediate stiffness in the ureter section.

9. The ureteral stent of claim 1, wherein a material durometer of the kidney section is in a range of 10 to 50 Shore A, and a material durometer of the bladder section is in a range of 50 to 90 Shore A.

* * * * *